United States Patent [19]

Davidson

[11] 4,315,380
[45] Feb. 16, 1982

[54] METHOD OF PROCESSING SEEDS OR CEREAL TO ACCELERATE NATURAL GERMINATION

[75] Inventor: Maxwell W. Davidson, Edinburgh, Scotland

[73] Assignee: Maxwell Davidson Limited, Edinburgh, Scotland

[21] Appl. No.: 100,742

[22] Filed: Dec. 6, 1979

[30] Foreign Application Priority Data

Jul. 22, 1976 [GB] United Kingdom ............... 30498/76
Jun. 13, 1978 [FR] France ................................ 78 17592
Jun. 20, 1978 [DE] Fed. Rep. of Germany ....... 2826907

[51] Int. Cl.³ ........................................... A01B 79/00
[52] U.S. Cl. .................................. 47/58; 47/DIG. 9; 435/93; 435/818
[58] Field of Search ................ 47/14, 16, 58, DIG. 9; 435/302, 303, 185, 246, 807, 812, 818, 315, 93

[56] References Cited

U.S. PATENT DOCUMENTS

| | | | |
|---|---|---|---|
| 2,038,451 | 4/1936 | Schattaneck | 435/818 |
| 2,891,892 | 6/1959 | Popp | 435/185 |
| 3,233,366 | 2/1966 | Nuttle et al. | 47/16 |
| 3,385,763 | 5/1968 | Bloch | 435/185 |
| 3,563,858 | 2/1971 | Worthington et al. | 435/818 |
| 3,853,713 | 12/1974 | Colclough | 435/303 |
| 3,957,585 | 5/1976 | Malick | 435/246 |
| 4,041,180 | 8/1977 | Wilson | 435/246 |

FOREIGN PATENT DOCUMENTS 1582052 4/1970 Fed. Rep. of Germany ... 47/DIG. 9
1583148 1/1981 United Kingdom .................. 47/58

*Primary Examiner*—James R. Feyrer
*Attorney, Agent, or Firm*—Mason, Fenwick & Lawrence

[57] ABSTRACT

The invention is concerned with a method of processing seeds or cereal to accelerate natural germination in which a bed of seeds or cereal are steeped in water which is oxygenated by circulation therethrough of a stream of oxygenated air, the temperature of the bed is controlled during steeping by cooling the circulating oxygenated air, the body of water is drained from the bed, oxygenated air is passed through the bed to dry the seeds or cereal, and the temperature of the bed is controlled during the drying step whereby the bed of seeds or cereal is pregerminated.

Advantages of the invention are that the seeds or cereal are in a condition ready for immediate germination when required but may be stored for a indefinite period of time. Also when the seeds or cereal are or is planted they can grow immediately since they have the correct moisture uptake, and further the germination and original growth phases are uniformly and actively promoted by the oxygenated reaction.

4 Claims, 7 Drawing Figures

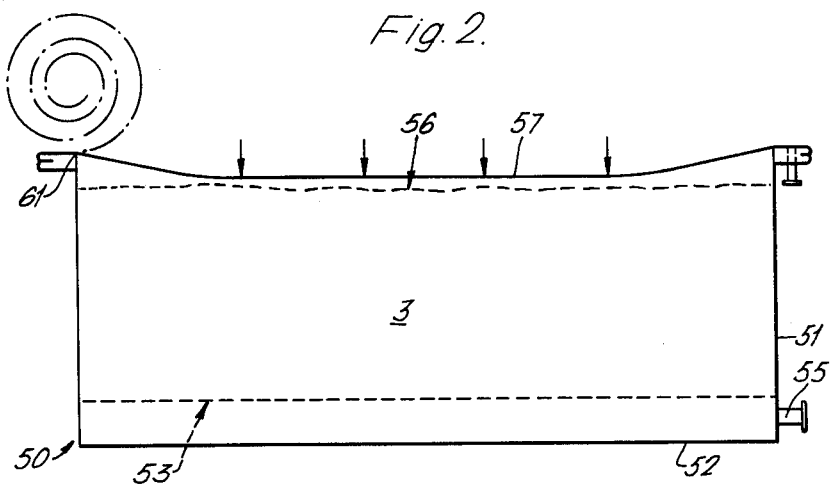
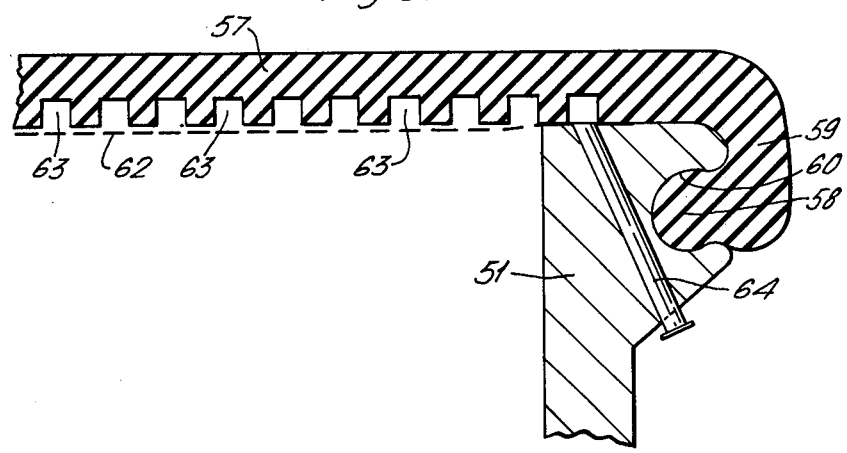
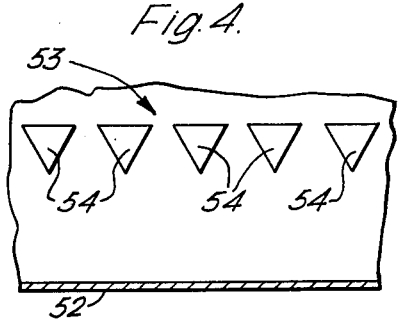

METHOD OF PROCESSING SEEDS OR CEREAL TO ACCELERATE NATURAL GERMINATION

The present invention relates to the treatment of seed and cereals to accelerate natural germination.

More particularly the invention relates to a process to accelerate natural germination of seed prior to planting or sowing in horticultural or agricultural processes and also to a process for the bulk treatment of cereals, such as barley, in which considerable masses of such cereals can be brought to a state for natural germination and sprouting for the purpose of producing malted barley.

The present invention is particularly but not exclusively concerned with the production of malted barley for use in the brewing of malted beverages.

It is beneficial during the several day long process required for the organic, enzymic and chemical changes to take place during germination, for the humidity, temperature, pressure, pH (hydrogen ion concentration) and surrounding atmosphere of the grains in bulk and individually to be kept under control so that the proper rate, efficiency of conversion, quality of product, uniformity of germination is achieved within the germination container, receptacle or plant.

In order to prepare seeds or cereals in a dry condition and in a state ready for natural germination, which can be stored and planted, or wetted and planted at a later date without undue degeneration of the seeds or cereals, it is necessary to prevent decomposition of the seeds or cereals prior to planting.

It has been proposed heretofore to prepare seeds for germination by covering the seeds with a layer of water over the surface of which is circulated a current of air or pure oxygen. The immersed seeds absorb oxygen dissolved in the water from the air or pure oxygen atmosphere, and the oxygen content of the water is rapidly reduced to a condition which does not permit final germination. When the water is agitated to replace the dissolved oxygen consumed by the seeds, this allows them to germinate without difficulty.

It is an object of the present invention to provide an improved process of accelerating natural germination of seed and particularly cereals.

According to the present invention there is provided a method of processing seeds or cereal to accelerate natural germination, comprising steeping a bed of seeds or cereal in a body of oxygenated water, controlling the temperature of the bed during the steeping, draining the body of water from the bed and pregerminating the seeds or cereal in a germination-promoting atmosphere of oxygenated air. By the term oxygenated air is meant air which contains not less than 33% of oxygen by volume, as well as pure oxygen.

The invention can be used for treating seeds of plants, grasses and cereals, prior to planting or sowing.

Embodiments of the present invention will now be described by way of example with reference to the accompanying drawings in which:

FIG. 2 shows schematically a second form of apparatus for carrying out the present invention;

FIG. 3 shows a portion of the top cover of the apparatus of FIG. 2 in greater detail;

FIG. 4 shows a further portion of the apparatus of FIG. 2 in greater detail;

Although in the presently described treatments pure oxygen is passed through a bed of seeds or cereal, it is possible to use oxygenated air. The treatment can be applied to (a) seeds or plants which are to be planted or sown and these can comprise for example, plant seeds, grass seeds or cereals, or (b) to cereals e.g. barley in the production of malted barley in the brewing of malted beverages.

The bed of seeds (or cereals) are steeped in water, and means are provided to dry the seeds after the oxygen treatment is completed. For the treatment (a) above it is suggested 0.02 lbs. of pure oxygen per hour be evenly applied to 100 lbs. of the plant seed or cereal, while for the treatment (b) 0.05 lbs. of pure oxygen are applied to 100 lbs. of cereal per hour.

Figure 1:
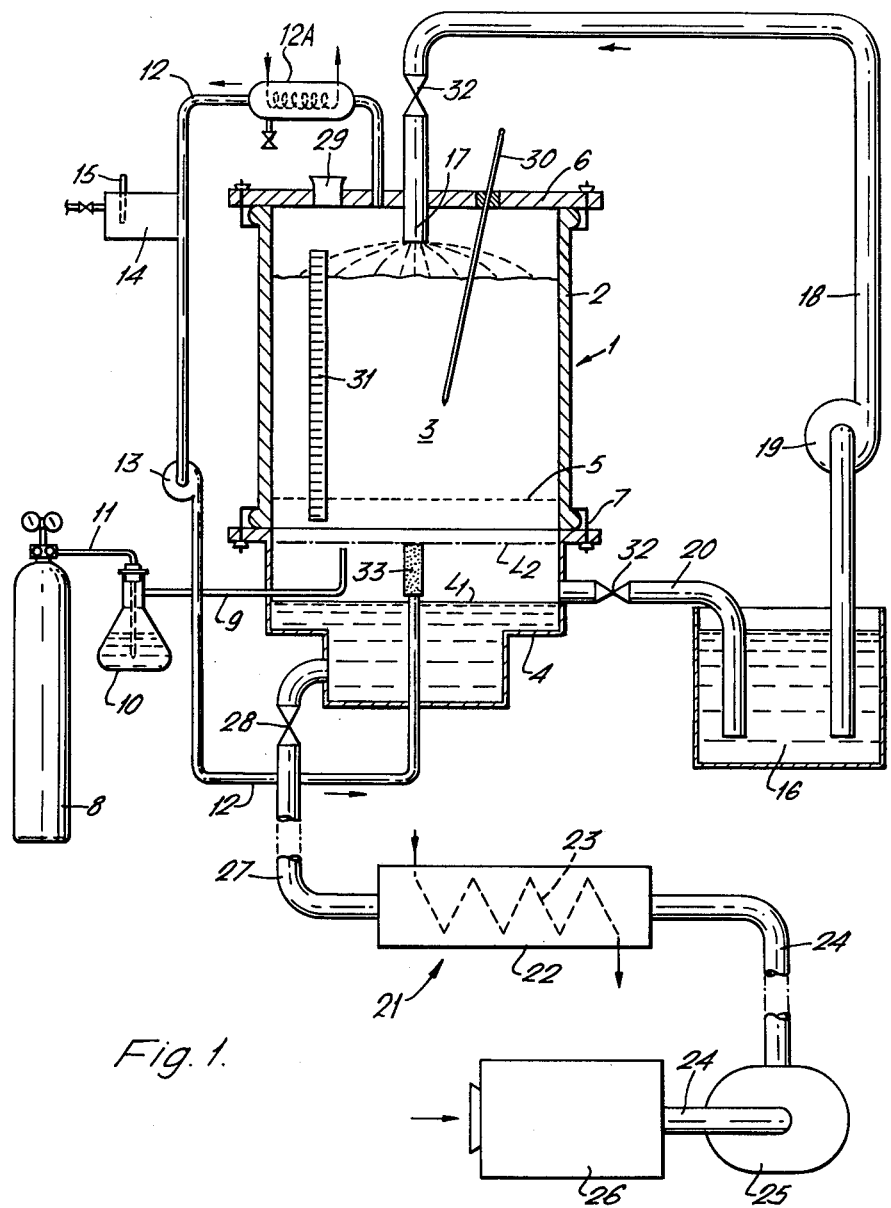
FIG. 1 shows schematically one form of apparatus for carrying out the present invention.

FIG. 1 shows a basic or pilot form of apparatus indicating a suitable layout of equipment for the pregermination of barley for the treatment (b) above according to the present invention. The apparatus comprises a vessel 1 including an upper part 2 housing a bed 3 of barley, and a lower sump 4 for water. The part 2 includes a lower perforated plate 5 to support the bed 3, and this part 2 can be made of glass, or metal or enamel lined metal. A removable lid 6 is fitted to the top of the vessel 1, and the sump 4 is fitted to part 2 by securing means 7 whereby with the perforated plate 5 removed the germinated barley bed 3 can be discharged from the vessel 1.

Pure oxygen from a suitable source such as oxygen cylinder 8 is discharged in the vessel 1 below plate 5 by means of supply pipe 9. The cylinder 8 includes means to control the oxygen flow, the oxygen being bubbled through water holder 10 by line 11 prior to supply to pipe 9. The oxygen passes upwards through bed 3, and a recycling pipeline 12 having recirculatory fan 13 recycles the discharge gases to the base of the vessel 1 below plate 5. A vacuum is created in the vessel by suitable means, for example a vacuum pump (not shown). The pipeline 12 includes a sampling branch portion 14 for Orsat and chromatographic sampling of gas. A recording thermocouple 15 for sensing the gas temperature is provided at branch 14. The line 9 (or other additional line) can serve for the supply of an inert gas to the vessel 1, e.g. $CO_2$ or nitrogen, in the place of oxygen at the stage of the process where pregermination of the barley has been completed and it is necessary to prevent further germination. The recycling pipeline 12 includes a cooler 12A.

Water from reservoir 16 is delivered to spray head 17 by conduit system 18 including pump 19, and is sprayed into the bed 3 for steeping of the barley and also to cool the bed.

Water descends to the sump 4 and overflow water is returned to reservoir 16 by pipeline 20: $L_1$ and $L_2$ indicate two possible controlled water levels in sump 4. A foaming agent is supplied to the water in reservoir 16 so that there is created a foam layer below the bed 3 in vessel 1, and the return end of pipeline 12 includes a porous aerator head 33 which serves to create the foam layer.

It is normally essential that the barley of bed 3 be dried after pregermination is completed, preferably to contain not less than 8% by weight of moisture, and to this end a kilning system 21 is provided comprising a heat exchanger 22 having a heating coil 23 supplied with a heating medium such as steam, and an air supply line 24 delivering air to the heat exchanger 22 for heating, the line 24 including an air blower 25 and also an air conditioner 26 at its inlet end. A discharge line 27 provided with closure valve 28 delivers heated air to the sump 4. For drying of the barley, water is firstly drained from the sump 4 and the valve 28 then opened to permit heated air to enter the sump 4 and permeate upwardly through the bed 3: the air can be discharged from vessel 1 via a cover bore which is closable by plug 29. The bed temperature is normally maintained steady by circulating oxygen through or over the bed. The temperature is then elevated in an atmosphere of oxygen which is circulated and temperature-controlled to place the barley in a condition ready, when required, for rapid malting.

If, however, the apparatus for carrying out the process is integrated, for example, with a brewery, it is not necessary to dry the barley. In this case, water is drained from the sump 4 and oxygen is admitted to the vessel 1 through the supply pipe 9 to pass through the bed of barley and to permeate the barley until the barley is in a condition ready for malting.

A thermometer 30 measures the bed temperature and a scale 31 can be provided to check the bed depth: pipelines 18, 20 include closure valves 32.

By way of example, the vessel 1 could contain a bed of between 10 to 100 tonnes.

In operation of the apparatus, a vacuum is created in the vessel 1, and the barley bed 3 is thereafter steeped with water from the spray head 17, a foam layer being subsequently formed below the bed 3. Pure oxygen from source 8 is caused to permeate upwardly through the bed 3, and oxygen discharged from the bed is recycled via pipeline 12, the temperature of the oxygen and of the bed being checked. An oxygen supply rate of approximately 0.2 lbs. per hour per ton barley could be provided. The barley is thereby caused to pregerminate, and once pregermination is complete the bed is normally dried by the kilning system 21.

By the above treatment, the barley can be malted in approximately 48 hours (including 12 hour steeping), and this compares with seven days presently required for malting. Additionally there is improved germination efficiency and less loss of malting products than previously.

Similar apparatus could be used for oxygen treatment of seeds of plants, grasses and cereals for planting or sowing.

Modified apparatus for malting barley according to the present invention is shown in FIG. 2 and comprises a container or vessel for use in the pregermination of barley grains for malting, having an open topped vessel 50 with rectangular arranged side walls 51 and a closed bottom 52, the vessel 50 being able to house a grain bed of 450–500 quarters of barley (each quarter equals approx. 445 lbs.). The container 50 is made from dense concrete, or metal and can have tiled or coated walls, and a false bottom 53 is provided in the form of triangular sectional ribs 54 (see FIG. 4) for extraction of gas and moisture during drying. A discharge 55 is provided from the vessel 50 below the false bottom 53. The vessel 50 can be made with compressed concrete walls having a better than 2% liquid take up on surface. The open top 56 of the vessel 50 is closed by a removable cover or diaphragm 57 made from flexible material such as natural or synthetic rubber. The diaphragm 57 is fitted in air-tight manner to the vessel 50, and this can be achieved by providing an inwardly facing bead 58 (see FIG. 3) on a skirt portion 59 of the diaphragm which bead 58 can be sprung into tight engagement with a correspondingly shaped peripheral groove 60 on the outer surface of the side walls 51. Conveniently the diaphragm 57 could be secured to one edge 61 of the vessel 50 and rolled into position for vessel closure whereupon the bead is sprung into its mating groove: FIG. 2 shows the diaphragm in the rolled condition in dashed lines. A perforated flexible screen or cloth 62 (FIG. 3) is located immediately below the diaphragm 57 and is pressed against the grain bed 3 by the flexible diaphragm 57 on the creation of a vacuum within the vessel 50. A parallel series of longitudinally extending grooves 63 are arranged on the lower surface of the diaphragm 57 and co-operate with the perforated sheet 62 during grain pressing to form ducting for fluid passage to or from the bed 3. These longitudinal grooves 63 can be linked by a transverse groove or grooves (not shown). Additionally, an inlet 64 is provided on the vessel to the ducting.

Figure 5:
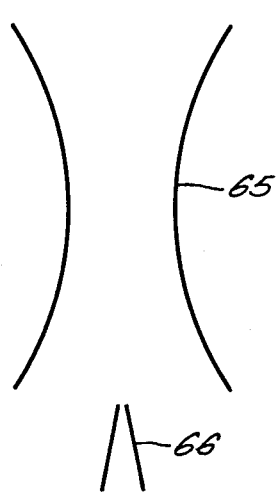
FIG. 5 shows a detail of means for turning grain or cereal in the apparatus of FIG. 2.
Figure 6:
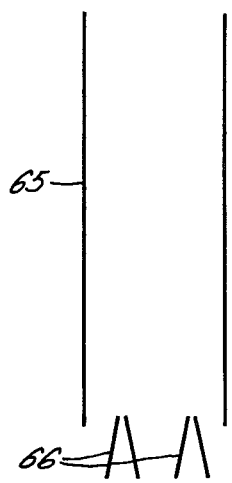
FIG. 6 shows a detail of alternative means for turning grain or cereal in the apparatus of FIG. 2.

The grains in the bed 3 can be lifted and turned using a conventional screw or auger device, but preferably an air lift turner (see FIGS. 5 and 6) is used comprising an open ended tube 65 for location in the grain bed 3 and a discharge inlet or inlets 66 for pressurised air discharging into one of the open ends of the tube 65. In this air turner arrangement, grains will be transported through the tube by the air flow and consequently a recirculation of grains will be achieved. A similar turner could be used in the bed 3 of the FIG. 1 apparatus.

Figure 7:
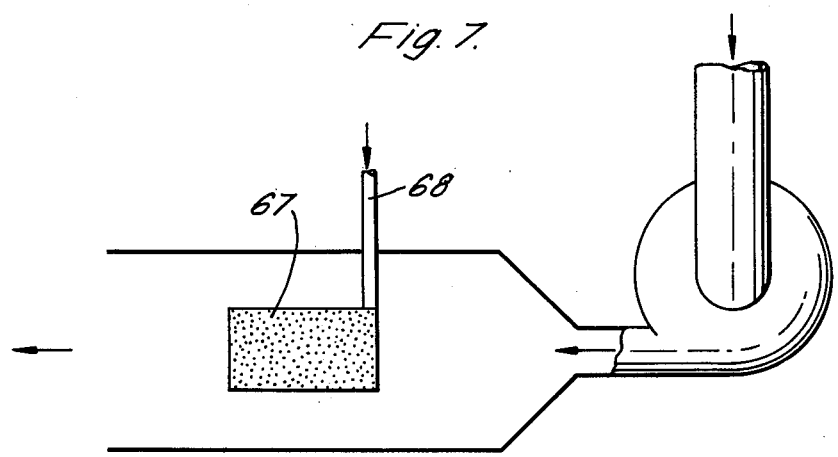
FIG. 7 shows a detail of a re-aerator arrangement for the apparatus of FIG. 2.

Further, means are provided for the re-ozygenation of the grain bed 3, which means can comprise a silica porous pot 67 (see FIG. 7) submerged in an aqueous solution being pumped through the grain bed 3 and a pressurised oxygen line 68 to the pot 67.

The apparatus of FIG. 2 operates generally similarly to that of FIG. 1. Specifically the barley grains are allowed to steep and then pregerminate for suitable periods (e.g. 2 to 3 days steeping and 4 to 6 days of pregermination). Additives such as Giberillic acid can be used. Again, pure oxygen is passed through the grain bed 3 during pregermination in place of the usual air. In particular, the oxygen can be drawn through the bed 3 from a suitable source via the inlet 64, the ducting 63 and the false bottom 53 by a suction effect in the discharge 55 whereby a vacuum is created in the vessel 50 causing the perforated cloth 62 to be pressed into the grain bed 3 by the diaphragm 57. The use of pure oxygen accelerates the pregermination process, and the consumption of pure oxygen is likely to be in the order of 12.8 lb. of oxygen per quarter of barley to achieve fully modified malted barley.

The use of the screen 62 and diaphragm 57 with ducts 63 enables more efficient delivery of oxygen to the bed 3 and facilitates the enclosing of large areas of malting streets without the necessity of resorting to rigid structure which would be expensive and unwieldy. Moreover it serves to squeeze and dewater the grain bed at the end of the malting process prior to drying.

Additionally, control apparatus can be provided to maintain or control the pressure and/or temperature within the vessel and the oxygen within the vessel can be conveniently changed or replaced with an inert gas, such as nitrogen or carbon dioxide, and can be at low pressure and under compression, with the addition of acidic and alkaline solutions, additives and inhibitor solutions (e.g. Giberillic acid).

Again, apparatus similar to that of FIG. 2 could be used for oxygen treatment of seeds or cereals prior to planting or sowing in agriculture and horticulture. The apparatus of FIGS. 1 and 2 can conveniently provide in the malting process:

(a) Steam sterilisation at elevated temperatures;
(b) Fan circulation with dry, heated or humid oxygen as required; and also the use of a refrigerated cooling system;
(c) Water or spray foam systems with atomiser;
(d) Chlorinated water circulation for sterilisation;
(e) Methyl disulphide (or similar) gaseous circulation for enclosed fumigation to kill off enzymes, bacteria and nematodes;
(f) Continuous oxygenation of steep water solutions by virtue of the porous pot arrangement;
(g) De-aerating by pressure/vacuum;
(h) Oxygen blowing to dry-displacement of water with oxygen;
(i) The use of potassium cyanide to innoculate respiratory functions of grains; and
(j) The use of oxidising agents.

A further characteristic of the arrangement is that sudden pressure release (as occurs at vacuum breakdown) causes grain cake breaking through eruptive expansion.

It will be understood that while pure oxygen has been referred to as being used in the embodiments described, oxygenated air as discussed earlier can be used in lieu of pure oxygen with substantially the same pregermination results on seeds or cereals.

An advantage of the invention is that in the case where the seeds or cereals are not required for immediate use steeping the seeds or cereals to the desirable moisture content in oxygenated water, maintaining a steady temperature by circulating oxygen or oxygenated air, draining the water, and then elevating the temperature to dry them in an atmosphere of pure oxygen or oxygenated air which is circulated and is temperature-controlled places the seeds or cereals in a condition ready for rapid germination when planted, or in the case of barley in a condition ready for rapid malting. Where the seeds or cereals are required for immediate use, and the drying stage is omitted, permeation of the seeds or cereals by oxygen or oxygenated air places the seeds or cereals in a condition ready for immediate use and rapid germination or malting as the case may be.

The required stage for stopping the process is when substantially all the necessary enzymes and other organic materials suitable for rootlet and plumule growth have been produced and the water barrier of the testa has been reduced, but before a rootlet growth has actually emerged from the testa. At this stage the growing points of the rootlets of the seeds or cereals can be seen clearly within the testa, all of which is assisted by the action of oxygen on the wetted seeds or cereals, the presence of oxygen preventing the growth of anaerobic bacteria and other organisms which could cause putrification. Another salient or critical feature is that the presence of pure oxygen or oxygenated air increases the rate of respiration within the structure of the seed or cereal itself. The chemical changes involved in the respiration are exothermic and the heat produced raises the internal temperature of the seeds or cereals and creates a temperature gradient from the centre of the seed or cereal outwards. As a result of this, the seeds or cereals in the presence of oxygen dry themselves progressively at a rapid rate even when the atmosphere surrounding them is fully saturated with water vapour.

The process therefore accelerates the natural pregermination stages because of the internal release of heat and it has been found that the treated seeds or cereal will germinate, when planted, at temperatures below those normally required for natural germination of untreated seeds or cereals. The drying stage when used, which provides for dry pure oxygen or oxygenated air to pass at an elevated temperature through the seeds or cereals, is therefore able to effect rapid drying in an aerobic atmosphere before an irreversible seed or cereal degeneration can take place. Where the drying stage is not used, the seeds or cereals are of course used before seed or cereal degeneration takes place.

Modifications are possible. For example in the FIG. 1 apparatus it could be arranged for the oxygen to flow downwardly through the bed, similarly as in FIG. 2 apparatus. in this case, the foam layer would be located above the bed.

In horticulture or agriculture, the pre-treatment of seeds or cereals with oxygen prior to planting or sowing enables the seeds or cereal to germinate in less than 24 hours. Additionally, when planted, the seeds can grow immediately since they have the correct moisture uptake, and further the germination and original growth phases are uniformally and actively promoted by the oxygen reaction. The invention will provide the following advantages in agriculture and horticulture:

1. Even and immediate growth after planting or sowing even with adverse weather conditions, temperature conditions, humidity or wetness of the soil.
2. Greater utilisation of land through more crops per year.
3. Lower or no dormancy of seeds or cereals due to oxygen effects.
4. Less insect or bird damage due to quicker rootlet growth whereby the vulnerability period is reduced.
5. Ability to store the pregerminated seeds or cereals for an indefinite period of time.

I claim:

1. A method of pregerminating seeds to break seed dormancy to accelerate sprouting at a later period comprising steeping a bed of seeds in a body of oxygenated water, controlling the temperature of the bed during the steeping, draining the body of water from the bed and holding the seeds in a gaseous atmosphere maintained with an oxygen content ranging from at least 33 to about 100% oxygen by volume whereby putrefaction of such seeds by the development of anaerobic conditions therein is prevented.

2. A method as claimed in claim 1 wherein the bed is cooled.

3. A method as claimed in claim 1 wherein the bed of seed or cereal is dried by passing therethrough a gas maintained at an oxygen content of at least 33 to about 100% by volume, the temperature of the bed being controlled during drying.

4. A method as claimed in claim 1 including placing the bed in a vacuum environment.

* * * * *